United States Patent
Chen et al.

(10) Patent No.: US 11,859,296 B2
(45) Date of Patent: Jan. 2, 2024

(54) METHOD FOR PRODUCING 2,5-FURANDICARBOXYLIC ACID (FDCA) BY ELECTROCATALYTIC OXIDATION OF 5-HYDROXYMETHYLFURFURAL (HMF) AND SIMULTANEOUSLY GENERATING HYDROGEN BY WATER ELECTROLYSIS

(71) Applicant: NINGBO INSTITUTE OF MATERIALS TECHNOLOGY & ENGINEERING, CHINESE ACADEMY OF SCIENCES, Ningbo (CN)

(72) Inventors: Chunlin Chen, Ningbo (CN); Zhenqiang Zhou, Ningbo (CN); Jian Zhang, Ningbo (CN)

(73) Assignee: NINGBO INSTITUTE OF MATERIALS TECHNOLOGY & ENGINEERING, CHINESE ACADEMY OF SCIENCES, Ningbo (CN)

( * ) Notice: Subject to any disclaimer, the term of this patent is extended or adjusted under 35 U.S.C. 154(b) by 0 days.

(21) Appl. No.: 17/762,116

(22) PCT Filed: Jun. 10, 2020

(86) PCT No.: PCT/CN2020/095323
§ 371 (c)(1),
(2) Date: Mar. 21, 2022

(87) PCT Pub. No.: WO2021/051897
PCT Pub. Date: Mar. 25, 2021

(65) Prior Publication Data
US 2022/0349070 A1    Nov. 3, 2022

(30) Foreign Application Priority Data
Sep. 20, 2019   (CN) .......................... 201910891734.6

(51) Int. Cl.
*C25B 3/05*    (2021.01)
*C25B 3/23*    (2021.01)
(Continued)

(52) U.S. Cl.
CPC .............. *C25B 3/05* (2021.01); *C07D 307/68* (2013.01); *C25B 1/04* (2013.01); *C25B 3/07* (2021.01);
(Continued)

(58) Field of Classification Search
CPC ........... C25B 3/05; C25B 3/23; C25B 11/065; C25B 11/077; C25B 11/067
(Continued)

(56) References Cited

U.S. PATENT DOCUMENTS

2018/0023199 A1    1/2018  Sun et al.

FOREIGN PATENT DOCUMENTS

| CN | 104953135 A | 9/2015 |
| CN | 105413730 A | 3/2016 |

(Continued)

OTHER PUBLICATIONS

Kang et al., "Electrocatalysis of 5-hydroxymethylfurfural at Cobalt Based Spinel Catalysts with Filamentous Nanoarchitecture in Alkaline Media," Applied Catalysis B: Environmental (Mar. 1, 2019), vol. 242, pp. 85-91. (Year: 2019).*
(Continued)

*Primary Examiner* — Edna Wong
(74) *Attorney, Agent, or Firm* — Bayramoglu Law Offices LLC

(57) ABSTRACT

A method for producing 2,5-furandicarboxylic acid (FDCA) by electrocatalytic oxidation of 5-hydroxymethylfurfural (HMF) is provided, where the catalytic oxidation is conducted using an electrolytic cell; the electrolytic cell is a three-electrode electrolytic cell or a two-electrode electro-
(Continued)

lytic cell; an anode used is a monolithic electrode; the monolithic electrode includes a carrier and a catalytically active substance loaded on the carrier; and the catalytically active substance includes cobaltosic oxide particle-encapsulated nitrogen-doped carbon nanowires. The method has high activity and high selectivity, and the anodic catalyst is highly tolerant to HMF.

11 Claims, 8 Drawing Sheets

(51) Int. Cl.
  *C25B 11/067* (2021.01)
  *C25B 11/077* (2021.01)
  *C25B 11/061* (2021.01)
  *C25B 3/07* (2021.01)
  *C25B 11/065* (2021.01)
  *C25B 11/054* (2021.01)
  *C25B 9/17* (2021.01)
  *C25B 11/091* (2021.01)
  *C07D 307/68* (2006.01)
  *C25B 1/04* (2021.01)

(52) U.S. Cl.
  CPC .................. *C25B 3/23* (2021.01); *C25B 9/17* (2021.01); *C25B 11/054* (2021.01); *C25B 11/061* (2021.01); *C25B 11/065* (2021.01); *C25B 11/091* (2021.01)

(58) Field of Classification Search
  USPC ........................................................ 205/427
  See application file for complete search history.

(56) References Cited

FOREIGN PATENT DOCUMENTS

| | | | | |
|---|---|---|---|---|
| CN | 106669762 A | | 5/2017 | |
| CN | 108130554 A | * | 6/2018 | ............... C25B 3/02 |
| CN | 108130554 A | | 6/2018 | |
| CN | 108160077 A | | 6/2018 | |
| CN | 108531936 A | | 9/2018 | |
| CN | 109599565 A | | 4/2019 | |
| CN | 109616669 A | | 4/2019 | |
| CN | 109837555 A | | 6/2019 | |
| CN | 109950555 A | * | 6/2019 | ............... C25B 3/23 |
| CN | 109950555 A | | 6/2019 | |
| CN | 110106514 A | | 8/2019 | |
| CN | 110205645 A | | 9/2019 | |

OTHER PUBLICATIONS

Zhao et al., "Highly Durable and Active Co3O4 Nanocrystals Supported on Carbon Nanotubes as Bifunctional Electrocatalysts in Alkaline Media," Applied Catalysis B: Environmental (Apr. 1, 2017), vol. 203, pp. 138-145. (Year: 2017).*

* cited by examiner

METHOD FOR PRODUCING 2,5-FURANDICARBOXYLIC ACID (FDCA) BY ELECTROCATALYTIC OXIDATION OF 5-HYDROXYMETHYLFURFURAL (HMF) AND SIMULTANEOUSLY GENERATING HYDROGEN BY WATER ELECTROLYSIS

CROSS REFERENCE TO THE RELATED APPLICATIONS

This application is the national phase entry of International Application No. PCT/CN2020/095323, filed on Jun. 10, 2020, which is based upon and claims priority to Chinese Patent Application No. 201910891734.6, filed on Sep. 20, 2019, the entire contents of which are incorporated herein by reference.

TECHNICAL FIELD

The present application relates to a method for producing 2,5-furandicarboxylic acid (FDCA) by electrocatalytic oxidation of 5-hydroxymethylfurfural (HMF) and simultaneously generating hydrogen by water electrolysis.

BACKGROUND

The increase in global energy consumption and the control of pollutant emissions in various countries make the demand for clean energy increasingly concerned. The development and utilization of hydrogen energy and biomass is considered as a feasible way to address the above-mentioned demand.

As one of the twelve biomass platform compounds recognized by the U.S. Department of Energy, FDCA has aromaticity and is structurally similar to terephthalic acid (TPA). Taking polycondensation with ethylene glycol (EG) as an example, bio-based poly(ethylene 2,5-furandicarboxylate) (PEF) derived from FDCA is superior to polyethylene terephthalate (PET) in terms of gas barrier performance, glass transition temperature, and mechanical performance. In addition, the consumption of non-renewable energy and the emission of greenhouse gases in the production of bio-based PEF are greatly reduced compared with those in the production of petroleum-based PET.

FDCA is usually prepared through catalytic oxidation of HMF in a liquid-phase system involving a catalyst. In order to accelerate the conversion, a noble metal catalyst is usually used to catalyze a reaction at a high temperature and a high oxygen pressure, which increases cost and also causes some safety problems. Moreover, mechanism studies show that the participation and activation of water molecules plays a key role in the conversion of HMF into FDCA. However, because water molecules can hardly be activated in a liquid-phase thermal catalysis process, the traditional liquid-solid phase reaction can hardly improve the energy utilization efficiency.

Electrocatalytic oxidation is a very promising technology with broad substrate tolerance, which enables the accurate control of a reaction depth through the adjustment of a potential window, involves low energy dissipation, and can be conducted at room temperature and normal pressure. The catalytic oxidation of alcohol aldehyde into a corresponding aldehyde or acid involves low activation energy, and thus the process can be achieved through electrochemical oxidation with low potential and low energy supply, which is a typical organic electro-oxidation reaction. Moreover, since a rate-controlling step of hydrogen production through water electrolysis is a four-electron anodic oxygen evolution reaction, which has a high energy barrier and leads to an oxygen product with a relatively low value. Therefore, the use of a low-potential organic electro-oxidation reaction to replace the anodic oxygen evolution reaction of water electrolysis helps to reduce a total reaction energy barrier of hydrogen production through water electrolysis and increase an overall reaction rate. In addition, there is no gaseous product at the anode, and the reaction does not require expensive proton exchange membranes or diaphragms to separate hydrogen and oxygen, thus can easily ensure the purity of hydrogen and avoid the risk of explosion of a hydrogen-oxygen mixture.

Therefore, developing a monolithic bifunctional catalyst with both HMF oxidation and hydrogen evolution properties and its application method can replace the anodic oxygen evolution reaction with a low potential HMF electro-oxidation to simultaneously produce high value-added products FDCA and hydrogen, improving the energy utilization efficiency. In addition, this method can be extended to other bio-based platform compounds and can further utilize distributed renewable electricity for reaction, which is of important theoretical and practical significance for the development of clean energy and the high-value utilization of biological resources.

SUMMARY

In order to solve the above technical problems, the present application provides a method for producing FDCA by electrocatalytic oxidation of HMF. The method has high activity and high selectivity, and an anodic catalyst is highly tolerant to HMF.

In order to achieve the above objective, the present application adopts the following technical solutions:

In an aspect of the present application, a method for producing FDCA by electrocatalytic oxidation of HMF is provided, where the electocatalytic oxidation is conducted using an electrolytic cell;
  the electrolytic cell is a three-electrode electrolytic cell or a two-electrode electrolytic cell, and an anodic catalyst used is a monolithic electrode;
  the monolithic electrode includes a carrier and an active substance loaded on the carrier; and the active substance includes cobaltosic oxide particle-encapsulated nitrogen-doped carbon nanowires.

Optionally, an electrolyte in the electrolytic cell may be an HMF-containing aqueous solution; and
  a concentration of HMF in the HMF-containing aqueous solution may be 0.001 mM to 500 mM.

Optionally, the electrolyte in the electrolytic cell may be an HMF-containing sodium hydroxide aqueous solution.

Optionally, an upper limit of the concentration of HMF in the HMF-containing aqueous solution may be selected from the group consisting of 0.1 mM, 1 mM, 5 mM, 10 mM, 30 mM, 50 mM, 100 mM, 150 mM, 200 mM, 250 mM, 300 mM, 350 mM, 400 mM, 450 mM, and 500 mM; and a lower limit of the concentration may be selected from the group consisting of 0 mM, 0.1 mM, 1 mM, 5 mM, 10 mM, 30 mM, 50 mM, 100 mM, 150 mM, 200 mM, 250 mM, 300 mM, 350 mM, 400 mM, and 450 mM.

Optionally, the electrolytic cell may have a voltage of 1.067 V to 2.0 V.

Optionally, the three-electrode electrolytic cell may have a minimum voltage of 1.067 V, and the two-electrode electrolytic cell may have a minimum voltage of 1.175 V.

Optionally, hydrogen may also be produced through water electrolysis in the electrolytic cell.

Optionally, the cathode may be at least one from the group consisting of the monolithic electrode, a graphite rod, a platinum sheet, a platinum wire, and a platinum mesh.

Optionally, the active substance may grow in situ on a surface of the carrier.

Optionally, the active substance may have a dendritic morphology formed by the cobaltosic oxide particle-encapsulated nitrogen-doped carbon nanowires.

Optionally, the carrier may be at least one from the group consisting of a metal foam, a carbon foam, and a carbon fiber sheet (CFS);

the cobaltosic oxide particle may have a particle size of 3 nm to 10 nm;

the nanowires each may have a diameter of 40 nm to 60 nm; and the nanowires may have a length of 500 nm of 2,000 nm.

Optionally, in the active material, a molar content of nitrogen may be 0.5% to 2%, a molar content of carbon may be 20% to 40%, and a molar content of cobalt may be 5% to 10%.

Optionally, an upper limit of the molar content of nitrogen in the active material may be selected from the group consisting of 1%, 1.5%, and 2%; and a lower limit of the molar content of nitrogen may be selected from the group consisting of 0.5%, 1%, and 1.5%.

Optionally, an upper limit of the molar content of cobalt in the active material may be selected from the group consisting of 6%, 7%, 8%, 9%, and 10%; and a lower limit of the molar content of cobalt may be selected from the group consisting of 5%, 6%, 7%, 8%, and 9%.

Another aspect of the present application is a preparation method of a monolithic cobaltosic oxide-encapsulated nitrogen-doped carbon nanowire catalyst growing in situ on a carrier, which has the characteristics of simple preparation, low cost, strong catalytic performance, long service life, and easy separation.

The preparation method of the monolithic catalyst includes the following steps:

S100: preparing an aqueous solution with a cobalt source, a nitrogen source, and a carbon source;

S200: immersing a carrier in the aqueous solution, and heating to allow a reaction to obtain a precursor; and S300: heating the precursor in an atmosphere of a protective gas to allow a reaction to obtain the monolithic catalyst.

Optionally, in S100, in the aqueous solution, cobalt in the cobalt source, nitrogen in the nitrogen source, carbon in the carbon source, and water may be in a molar ratio of 1:(3-10):(1.5-50):(600-1,200).

Optionally, the cobalt source may be at least one from the group consisting of $CoF_2$, $CoCl_2$, $CoBr_2$, $CoI_2$, $CoCO_3$, $Co(NO_3)_2$, and $CoSO_4$;

the nitrogen source may be at least one from the group consisting of urea and tetrasodium ethylenediaminetetraacetic acid (EDTA); and the carbon source may be at least one from the group consisting of urea and tetrasodium EDTA.

Optionally, in S200, the heating may be conducted at 110° C. to 160° C. for 8 hours to 24 hours;

in S200, the carrier may be immersed in the aqueous solution, heated to allow a reaction, washed, and dried to obtain the precursor;

the washing may be conducted as follows: rinsing 2 to 3 times successively with water and ethanol; and the drying may be conducted at 60° C. to 80° C. for 8 hours to 12 hours.

Optionally, in S300, the protective gas may be at least one from the group consisting of nitrogen, argon, and helium; and a flow rate of the protective gas may be 100 mL/min to 180 mL/min.

Optionally, in S300, the heating may be conducted at 300° C. to 400° C. for 0.5 hours to 1 hour.

Optionally, in S300, the heating may be conducted as follows: heating from room temperature to 300° C. to 400° C. at a heating rate of 4° C./min to 8° C./min, holding at the temperature for 0.5 hours to 1 hour, and cooling to room temperature at a cooling rate of 2° C./min to 3° C./min.

In the present application, "HMF" is an abbreviation for 5-hydroxymethylfurfural, "FDCA" is an abbreviation for 2,5-furandicarboxylic acid, "FFCA" is an abbreviation for 5-formyl-2-furancarboxylic acid, "DFF" is an abbreviation for 2,5-diformylfuran, and "HMFCA" is an abbreviation for 5-hydroxymethyl-2-furancarboxylic acid.

The present application has the following beneficial effects:

1) In the three-electrode system used in the method for producing FDCA by electrocatalytic oxidation of HMF provided in the present application, a monolithic cobaltosic oxide-encapsulated nitrogen-doped carbon nanowire catalyst is adopted as an anodic catalyst, which shows excellent performance in both oxygen evolution by water electrolysis without HMF and electrocatalytic oxidation of HMF to prepare FDCA, and can tolerate the feed of high-concentration HMF.

2) In the three-electrode system of the method for producing FDCA by electrocatalytic oxidation of HMF provided in the present application, a monolithic cobaltosic oxide-encapsulated nitrogen-doped carbon nanowire catalyst is adopted as an cathodic catalyst, which shows excellent performance in hydrogen evolution by water electrolysis, and the addition of HMF to the electrolyte does not affect the hydrogen production performance.

3) In the method for producing FDCA by electrocatalytic oxidation of HMF provided in the present application, a two-electrode symmetric electrolytic cell is assembled to simultaneously conduct the electrocatalytic oxidation of HMF to FDCA and the water electrolysis to hydrogen, which requires an overpotential 362 mV lower than that of simple water electrolysis, indicating a better catalytic performance with lower required energy compared to simple water electrolysis.

4) In the method for producing FDCA by electrocatalytic oxidation of HMF provided in the present application, the catalyst is used to prepare FDCA through electrocatalytic oxidation of HMF, which shows very high FDCA selectivity and leads to high product purity. Moreover, the faradaic efficiency is close to 100%, with almost no energy waste.

5) The monolithic catalyst provided in the present application (namely, a monolithic cobaltosic oxide-encapsulated nitrogen-doped carbon nanowire catalyst) has a macroscopic morphology and a hierarchical structure, and can provide a structural strength and an effective mass transfer channel for a reactant suitable for practical applications. In addition, the carbon encapsulation design can block the corrosion of acid and alkali to exposed metals, prolong a service life of the catalyst, and build a confined space. The nitrogen doping can increase the local electron cloud density on a carbon surface and improve the catalytic performance. Compared with a cobalt-based powder catalyst, the monolithic catalyst is easier to be separated after use.

6) A catalyst prepared by the preparation method of the monolithic cobaltosic oxide-encapsulated nitrogen-doped carbon nanowire catalyst provided by the present application has high catalytic efficiency, strong catalytic stability, and long service life, and is easy to be separated from a product after use.

DETAILED DESCRIPTION OF THE EMBODIMENTS

Figure 1:
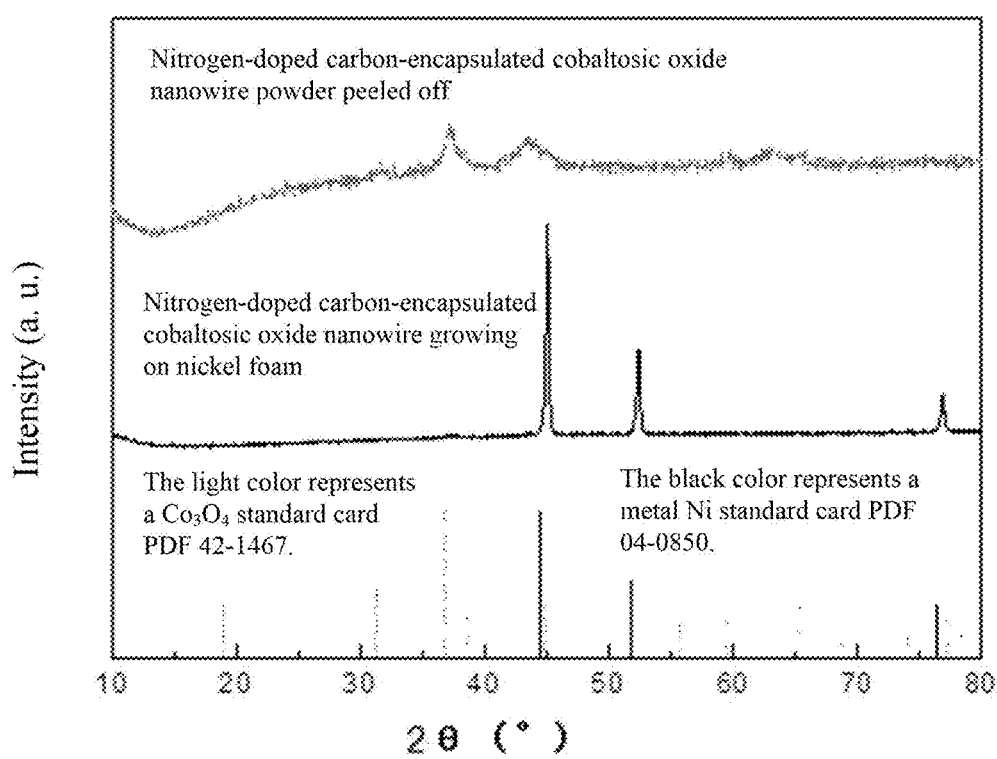
FIG. 1 shows X-ray diffractometry (XRD) patterns of the monolithic cobaltosic oxide-encapsulated nitrogen-doped carbon nanowire catalyst prepared in Example 1 of the present application and surface peelings thereof.

The present application will be described in detail below with reference to examples, but the present application is not limited to these examples.

Unless otherwise specified, the raw materials and carriers in the examples of the present application are all purchased from commercial sources.

Analysis methods in the examples of the present application are as follows:

The XRD analysis is conducted using a Bruker D8 DISCOVER X-ray diffractometer with Cu as a target.

The SEM analysis is conducted using a HITACHI S-4800 scanning electron microscope at 8.0 kV.

The TEM analysis is conducted using an FEI F20 transmission electron microscope at 200 kV.

The XPS analysis is conducted using a Kratos AXIS ULTRA$^{DLD}$ device with Al as a target.

The ICP analysis is conducted using an SPECTRO ARCOS ICP-OES instrument.

A method for producing FDCA by electrocatalytic oxidation of HMF is provided, where the catalytic oxidation is conducted using an electrolytic cell;
the electrolytic cell is a three-electrode electrolytic cell or a two-electrode electrolytic cell;
an anodeused is a monolithic catalyst;
the monolithic catalyst includes a carrier and an active substance loaded on the carrier; and
the active substance includes cobaltosic oxide particle-encapsulated nitrogen-doped carbon nanowires.

A preparation method of the monolithic catalyst includes the following steps:

S100: Preparation of a solution: $Co(NO_3)_2$ is mixed with a nitrogen-containing compound and a carbon-containing compound in a specified ratio, and then water is added to obtain the solution, where the $Co(NO_3)_2$, the nitrogen-containing compound, and the carbon-containing compound may be in a molar ratio of 1:(1.5-1):5.

Preferably, as an available embodiment, the nitrogen-containing compound and the carbon-containing compound may each be one or both from the group consisting of urea and tetrasodium EDTA.

The present application has no specific limitations on a concentration of the prepared solution. In order to prepare a monolithic cobaltosic oxide-encapsulated nitrogen-doped carbon nanowire catalyst with excellent performance, enhance its catalytic stability, and prolong its service life, preferably, a molar ratio of $Co(NO_3)_2$ to water may be 1:600 to 1:1200.

S200: Hydrothermal reaction: The solution obtained in step S100 is placed in a reaction kettle, and a carrier such as a metal foam, a carbon foam, or a CFS is added, kept at 110° C. to 160° C. for 8 hours to 24 hours, washed, and dried to obtain a precursor.

In S200, there is no special limitation on the added carrier such as a metal foam, a carbon foam, or a CFS. In order to prepare a uniform catalyst and improve its catalytic efficiency, preferably, a specification of carrier such as a metal foam, a carbon foam, or a CFS may allow the carrier to be immersed in the solution.

In this step, the precursor is obtained through a hydrothermal reaction, and the hydrothermal reaction may be conducted at 110° C. to 160° C. for 8 hours to 24 hours.

A surface of the precursor obtained by the hydrothermal reaction is covered with a small amount of precipitate. In order to remove the precipitate, a washing operation is required. Preferably, the washing may be conducted as follows: washing the precursor 2 to 3 times successively with water and ethanol.

After the precursor is rinsed, a drying operation is required to remove residual water and ethanol. Preferably, the drying may be conducted at 60° C. to 80° C. for 8 hours to 12 hours.

S300: Carbonization: The precursor obtained in S200 is placed in a heating furnace, a protective gas is introduced, and the precursor is kept at 300° C. to 400° C. for 0.5 hours to 1 hour and then cooled to obtain the monolithic cobaltosic oxide-encapsulated nitrogen-doped carbon nanowire catalyst.

In this step, the target monolithic cobaltosic oxide-encapsulated nitrogen-doped carbon nanowire catalyst is obtained through a carbonization process. In order to facilitate the introduction of the protective gas, the heating furnace may preferably be a tube furnace with a built-in quartz tube or corundum tube, and the protective gas may preferably be one or more from the group consisting of nitrogen, argon, and helium. A flow rate of the protective gas should not be too high, and may preferably be 100 mL/min to 180 mL/min. This flow rate can prevent the product from ablation and ensure the purity of the product, thereby improving the physical and chemical properties of the product.

In S300, the heating may be conducted by a one-step heating method. In order to ensure the quality of the product, a heating rate should not be too high. Preferably, a temperature control process of the heating furnace may be as follows: heating from room temperature to 300° C. to 400° C. at a heating rate of 4° C./min to 8° C./min, holding at the temperature for 0.5 hours to 1 hour, and cooling to room temperature at a cooling rate of 2° C./min to 3° C./min.

In the present application, the nitrogen-containing compound and the carbon-containing compound are added to provide an N source and a C source to form a nitrogen-doped carbon encapsulating layer, which reduces the corrosion of acid and alkali to cobalt and prolongs a service life of the catalyst.

It should be noted that, in the monolithic cobaltosic oxide-encapsulated nitrogen-doped carbon nanowire catalyst finally obtained, a load of Co and a doping concentration of N can be adjusted by adjusting an initial ratio of the raw materials.

The preparation of the monolithic cobaltosic oxide-encapsulated nitrogen-doped carbon nanowire catalyst of the present application adopts a simple operation method, shows low requirements for device and technology, involves common chemical raw materials, and has a low cost. In the catalyst obtained by the method of the present application, the N distribution is uniform, and the load of Co and the doping concentration of N can be adjusted, such that the catalyst can be used under different conditions. The monolithic cobaltosic oxide-encapsulated nitrogen-doped carbon nanowire catalyst obtained by the present application has a relatively high content of doped carbon with excellent conductivity, which works together with cobaltosic oxide nanowires to make the catalyst have high conductivity and long service life. In addition, compared with the nanopowder catalyst, the monolithic catalyst prepared by this method has more mass transfer channels and is easier to be separated from a catalysis product after use.

EXAMPLE 1

(1) 0.584 g of $Co(NO_3)_2 \cdot 6H_2O$, 0.6 g of urea, and 36 mL of deionized water were added to a beaker, and a resulting mixture was thoroughly stirred at room temperature. A molar ratio of the $Co(NO_3)_2$ to the urea was 1:5, and a molar ratio of the $Co(NO_3)_2$ to the water was 1:1,000.

(2) The solution prepared in step (1) was transferred to a 100 mL reactor, a nickel foam carrier was added and immersed in the solution, and the reactor was then placed in an oven to allow a reaction at 120° C. for 8 hours; after reaction, the carrier was taken out, rinsed twice successively with water and ethanol, placed in a beaker, and dried at 60° C. for 12 hours in an oven to obtain a precursor.

(3) The precursor obtained in step (2) was placed in a quartz boat of a tube furnace, then the tube furnace was sealed, and high-purity nitrogen was introduced as a whole-process protective gas at a flow rate of 150 mL/min for 30 min; and then the precursor was heated to 350° C. at a heating rate of 5° C./min, kept at the temperature for 0.5 hours, and then cooled to room temperature at a cooling rate of 3° C./min to obtain a monolithic cobaltosic oxide-encapsulated nitrogen-doped carbon nanowire catalyst growing on the nickel foam, which was denoted as sample 1.

EXAMPLE 2

(1) 0.584 g of $Co(NO_3)_2 \cdot 6H_2O$, 0.2 g of urea, and 36 mL of deionized water were added to a beaker, and a resulting mixture was thoroughly stirred at room temperature. A molar ratio of the $Co(NO_3)_2$ to the urea was 1:1.67, and a molar ratio of the $Co(NO_3)_2$ to the water was 1:1,000.

(2) This step was the same as in Example 1.

(3) This step was the same as in Example 1, and a product was denoted as Sample 2.

Compared with Example 1, the mass of urea among the raw materials used in this example was reduced, and the remaining preparation conditions remained unchanged. As the mass of urea decreases, the nitrogen-doped carbon encapsulating layer of the catalyst finally obtained becomes thinner and the amount of doped nitrogen decreases.

EXAMPLE 3

(1) This step was the same as in Example 1.

(2) The solution prepared in step (1) was transferred to a 100 mL reactor, a nickel foam carrier was added and immersed in the solution, and the reactor was then placed in an oven to allow a reaction at 140° C. for 8 hours; and then the carrier was taken out, rinsed twice successively with water and ethanol, placed in a beaker, and dried at 60° C. for 12 hours in an oven to obtain a precursor.

(3) This step was the same as in Example 1, and a product was denoted as Sample 3.

Compared with Example 1, a temperature of the hydrothermal reaction used in this example rose, and the remaining preparation conditions remained unchanged. As the temperature of the hydrothermal reaction rises, a nanowire diameter of the cobaltosic oxide-encapsulated nitrogen-doped carbon nanowire catalyst becomes larger.

EXAMPLE 4

(1) 0.3 g of $Co(NO_3)_2 \cdot 6H_2O$, 0.124 g of urea, and 20 mL of deionized water were added to a beaker, and a resulting mixture was thoroughly stirred at room temperature. A molar ratio of the $Co(NO_3)_2$ to the urea was 1:2, and a molar ratio of the $Co(NO_3)_2$ to the water was 1:1,078.

(2) The solution prepared in step (1) was transferred to a 100 mL reactor, a CFS carrier was added and immersed in the solution, and the reactor was then placed in an oven to allow a reaction at 120° C. for 12 hours; and then the carrier was taken out, rinsed twice successively with water and ethanol, placed in a beaker, and dried at 60° C. for 12 hours in an oven to obtain a precursor.

(3) The precursor obtained in step (2) was placed in a quartz boat of a tube furnace, then the tube furnace was sealed, and high-purity argon was introduced as a whole-process protective gas at a flow rate of 120 mL/min for 40 min; and then the precursor was heated to 350° C. at a heating rate of 5° C./min, kept at the temperature for 0.5 hours, and then cooled to room temperature at a cooling rate of 2° C./min to obtain a monolithic cobaltosic oxide-encapsulated nitrogen-doped carbon nanowire catalyst growing on the CFS, which was denoted as sample 4.

EXAMPLE 5

(1) 0.584 g of $Co(NO_3)_2 \cdot 6H_2O$, 0.8 g of $Na_4EDTA \cdot 4H_2O$, and 36 mL of deionized water were added to a beaker, and a resulting mixture was thoroughly stirred at room temperature. A molar ratio of the $Co(NO_3)_2$ to the $Na_4EDTA \cdot 4H_2O$ was 1:1.77, and a molar ratio of the $Co(NO_3)_2$ to the water was 1:1,000.

(2) The solution prepared in step (1) was transferred to a 100 mL reactor, a carbon foam carrier was added and immersed in the solution, and the reactor was then placed in an oven to allow a reaction at 130° C. for 8 hours; and then the carrier was taken out, rinsed twice successively with water and ethanol, placed in a beaker, and dried at 60° C. for 12 hours in an oven to obtain a precursor.

(3) The precursor obtained in step (2) was placed in a quartz boat of a tube furnace, then the tube furnace was sealed, and high-purity argon was introduced as a whole-process protective gas at a flow rate of 140 mL/min for 30 min; and then the precursor was heated to 400° C. at a heating rate of 5° C./min, kept at the temperature for 0.5 hours, and then cooled to room temperature at a cooling rate of 3° C./min to obtain a monolithic cobaltosic oxide-encapsulated nitrogen-doped carbon nanowire catalyst growing on the carbon foam, which was denoted as sample 5.

EXAMPLE 6

Samples 1 and 5 and cobaltosic oxide-encapsulated nitrogen-doped carbon nano-powders mechanically peeled off from the carriers were subjected to an XRD test. FIG. 1 shows XRD patterns of sample 1 and a cobaltosic oxide-encapsulated nitrogen-doped carbon nanowire powder mechanically peeled off from the nickel foam carrier. It can be seen from the figure that, the powder sample peeled off shows obvious diffraction peaks at 2-Theta angles of 31.27 (2 2 0), 36.85 (3 1 1), 44.81 (4 0 0), 59.36 (5 1 1), and 65.24 (4 4 0), which belong to the characteristic peaks of cobaltosic oxide. Due to the XRD signal of the cobaltosic oxide-encapsulated nitrogen-doped carbon nanowire layer growing on the nickel foam is far inferior to the signal intensity of the metal nickel carrier, the XRD signal of the sample 1 only reflects the signal of the nickel foam with only a weak signal of cobaltosic oxide at 2-Theta=36.85.

Samples 2 and 3 and cobaltosic oxide-encapsulated nitrogen-doped carbon nano-powders mechanically peeled off from the nickel foam were subjected to an XRD test. Compared with FIG. 1, there is only a difference in peak intensity, and the characteristic peaks are consistent.

Sample 4 and a cobaltosic oxide-encapsulated nitrogen-doped carbon nano-powder mechanically peeled off from the CFS were subjected to an XRD test. The cobaltosic oxide-encapsulated nitrogen-doped carbon nano-powder peeled off from the CFS is different from the cobaltosic oxide-encapsulated nitrogen-doped carbon nano-powder peeled off in FIG. 1 only in peak intensity, which have consistent characteristic peaks. Sample 5 and a cobaltosic oxide-encapsulated nitrogen-doped carbon nano-powder mechanically peeled off from the carbon foam were subjected to an XRD test. The cobaltosic oxide-encapsulated nitrogen-doped carbon nano-powder peeled off from the carbon foam is different from the cobaltosic oxide-encapsulated nitrogen-doped carbon nano-powder peeled off in FIG. 1 only in peak intensity, which have consistent characteristic peaks.

EXAMPLE 7

Figure 2A:
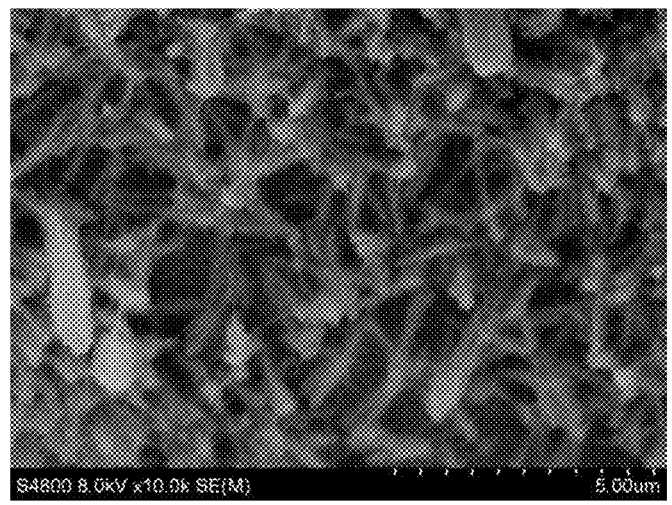
FIG. 2A shows a scanning electron microscopy (SEM) image of the monolithic cobaltosic oxide-encapsulated nitrogen-doped carbon nanowire catalyst prepared in Example 1 of the present application under a scale bar of 5 μm.
Figure 2B:
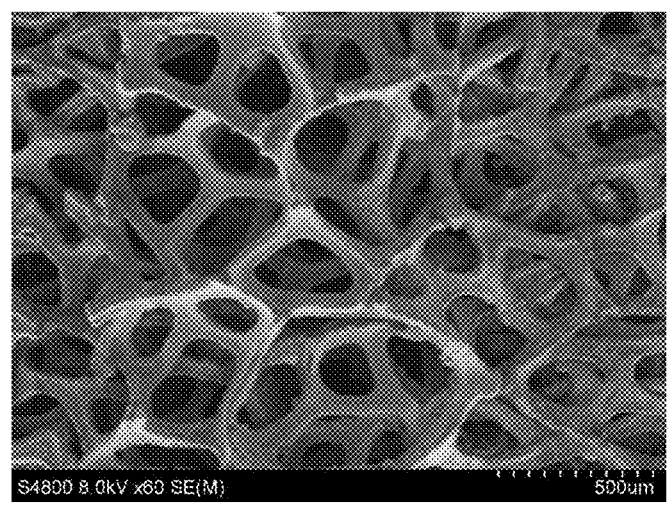
FIG. 2B shows an SEM image of the monolithic cobaltosic oxide-encapsulated nitrogen-doped carbon nanowire catalyst prepared in Example 1 of the present application under a scale bar of 500 μm.
Figure 2C:
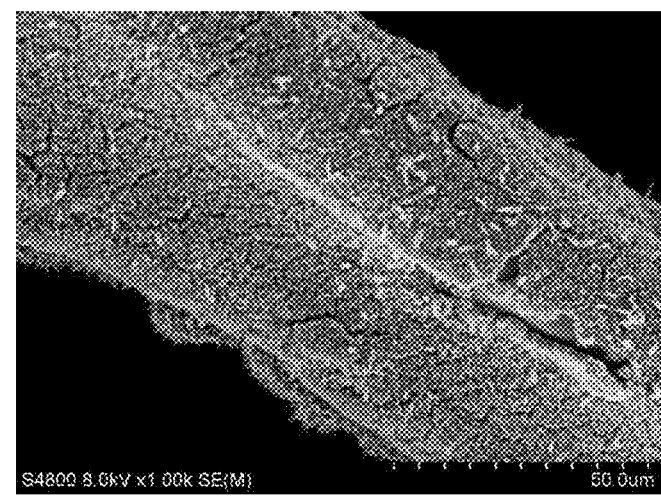
FIG. 2C shows an SEM image of the monolithic cobaltosic oxide-encapsulated nitrogen-doped carbon nanowire catalyst prepared in Example 1 of the present application under a scale bar of 50 μm.
Figure 3A:
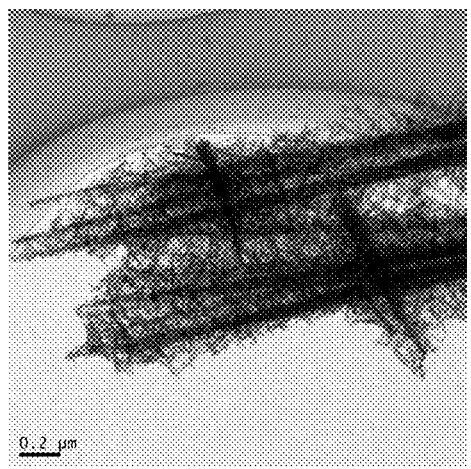
FIG. 3A shows a transmission electron microscopy (TEM) image of surface peelings of the monolithic cobaltosic oxide-encapsulated nitrogen-doped carbon nanowire catalyst prepared in Example 1 of the present application under a scale bar of 0.2 μm.
Figure 3B:
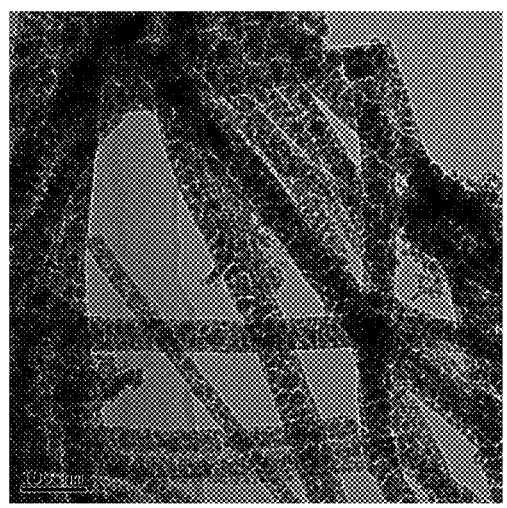
FIG. 3B shows a TEM image of surface peelings of the monolithic cobaltosic oxide-encapsulated nitrogen-doped carbon nanowire catalyst prepared in Example 1 of the present application under a scale bar of 100 nm.
Figure 3C:
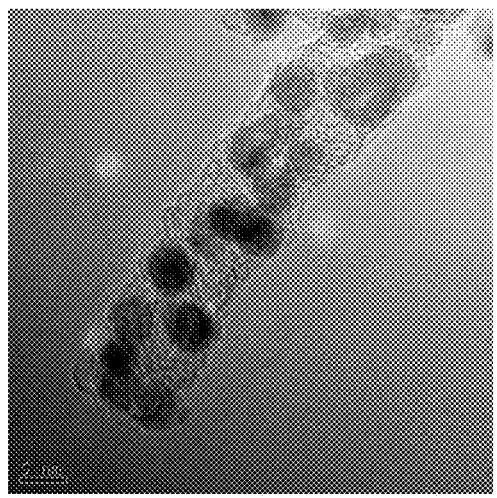
FIG. 3C shows a TEM image of surface peelings of the monolithic cobaltosic oxide-encapsulated nitrogen-doped carbon nanowire catalyst prepared in Example 1 of the present application under a scale bar of 5 nm.

Samples 1 and 5 and cobaltosic oxide-encapsulated nitrogen-doped carbon nano-powders mechanically peeled off from the carriers were subjected to SEM and TEM tests. FIG. 2A-FIG. 2C show SEM images of the monolithic cobaltosic oxide-encapsulated nitrogen-doped carbon nanowire catalyst growing on the nickel foam obtained in Example 1, and it can be seen from the figures that the catalyst has a pine branch-like microstructure. FIG. 3A-FIG. 3C show TEM images of the cobaltosic oxide-encapsulated nitrogen-doped carbon nanowire catalyst mechanically peeled off obtained in Example 1, and it can be seen from the figure that, the catalyst has a nanowire diameter of about 50 nm and a length of greater than 500 nm.

SEM and TEM images of Samples 2 and 3 and cobaltosic oxide-encapsulated nitrogen-doped carbon nano-powders mechanically peeled off from the carriers are similar to that of Sample 1, which are different only in nanowire diameter.

SEM and TEM images of Samples 4 and 5 and cobaltosic oxide-encapsulated nitrogen-doped carbon nano-powders mechanically peeled off from the carriers are similar to that of Sample 1, which are different only in carrier and nanowire diameter.

EXAMPLE 8

Figure 4:
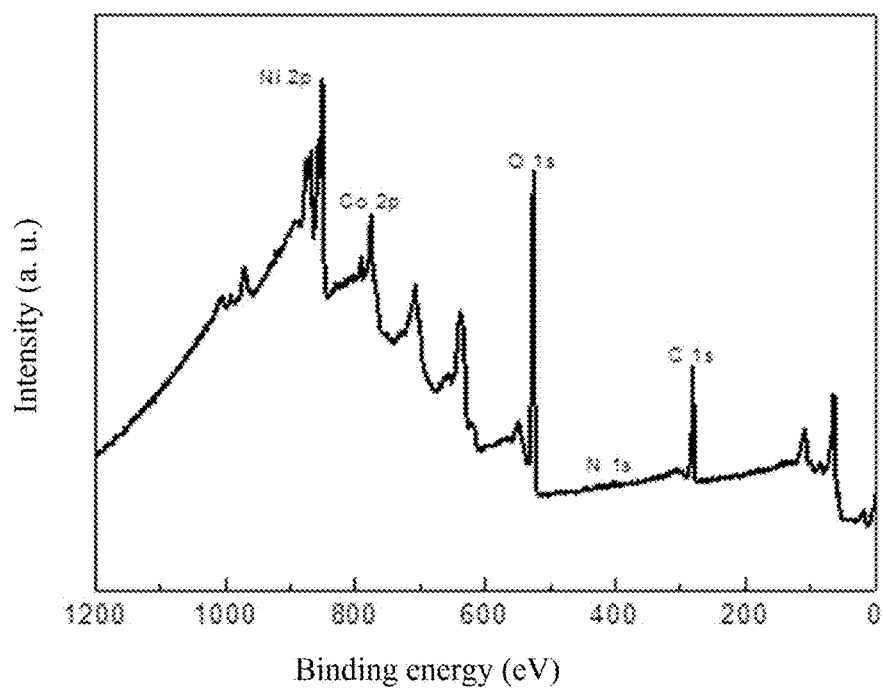
FIG. 4 is an X-ray photoelectron spectroscopy (XPS) spectrum of the monolithic cobaltosic oxide-encapsulated nitrogen-doped carbon nanowire catalyst prepared in Example 1 of the present application.
Figure 5A:
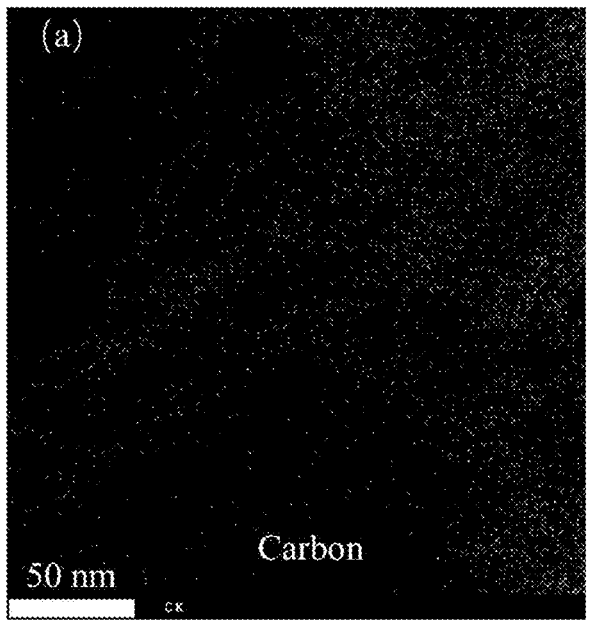
FIG. 5A shows a scanning transmission electron microscopy (STEM) element distribution map of the monolithic cobaltosic oxide-encapsulated nitrogen-doped carbon nanowire catalyst prepared in Example 1 of the present application for carbon.
Figure 5B:
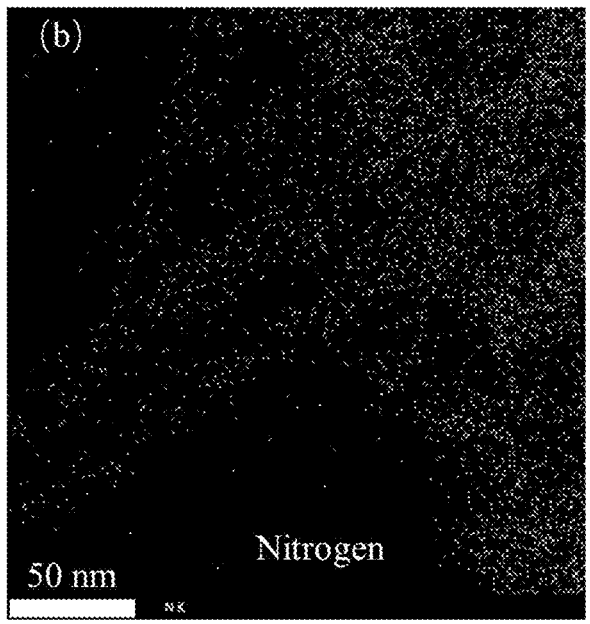
FIG. 5B shows a STEM element distribution map of the monolithic cobaltosic oxide-encapsulated nitrogen-doped carbon nanowire catalyst prepared in Example 1 of the present application for nitrogen.
Figure 5C:
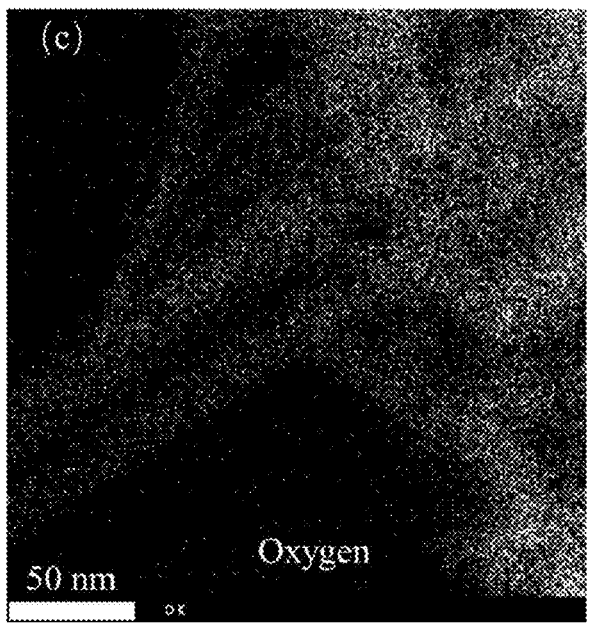
FIG. 5C shows a STEM element distribution map of the monolithic cobaltosic oxide-encapsulated nitrogen-doped carbon nanowire catalyst prepared in Example 1 of the present application for oxygen.
Figure 5D:
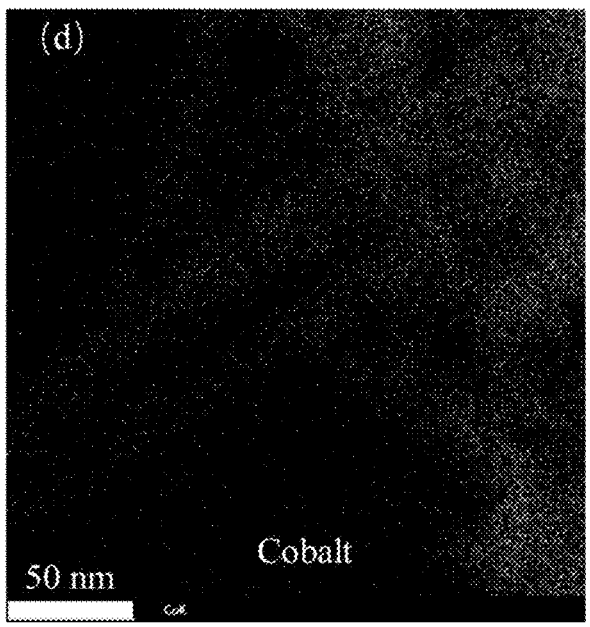
FIG. 5D shows a STEM element distribution map of the monolithic cobaltosic oxide-encapsulated nitrogen-doped carbon nanowire catalyst prepared in Example 1 of the present application for cobalt.

Samples 1 to 5 and cobaltosic oxide-encapsulated nitrogen-doped carbon nano-powders mechanically peeled off from the carriers were subjected to an XPS test. FIG. 4 is an XPS spectrum of sample 1 in Example 1. The results show that a percentage content of each element on the surface of the catalyst is as follows: C (37.65 at %), N (1.08 at %), Co (7.27 at %), and carrier nickel; and a total cobalt content determined by an inductively coupled plasma source mass spectrometer (ICP) is 20.1 at %. Therefore, it can be proved that cobalt is actually encapsulated by the nitrogen-doped carbon layer in the form of $Co_3O_4$.

Samples 1 to 5 and cobaltosic oxide-encapsulated nitrogen-doped carbon nano-powders mechanically peeled off from the carriers were subjected to a STEM test to obtain STEM element distribution maps. FIG. 5A-FIG. 5D show STEM element distribution maps of Sample 1 in Example 1, indicating that carbon, nitrogen, oxygen, and cobalt elements are uniformly distributed.

EXAMPLE 9

Working electrode fabrication: Samples 1 to 5 and pure nickel foam were each fixed by stainless steel electrode clamps to obtain working electrodes.

Counter electrode: A graphite rod, a platinum wire, or another inert conductive material was directly used as a counter electrode.

Three-electrode system assembly: The working electrode was used as anode, the counter electrode was used as cathode, and a saturated calomel electrode was used as a reference electrode; the electrodes were fixed in a rubber stopper and then fixed on a 100 mL reactor.

Two-electrode symmetrical electrolytic cell: the anode and cathode were two identical working electrodes, and a reactor had a volume of 10 mL or more.

Under normal temperature and normal pressure conditions, the assembled two-electrode system was subjected to an electrocatalytic performance test, with sodium hydroxide aqueous solution, a 10 mM HMF-containing sodium hydroxide aqueous solution, a 100 mM HMF-containing sodium hydroxide aqueous solution, and a 200 mM HMF-containing sodium hydroxide aqueous solution as electrolytes.

Figure 6:
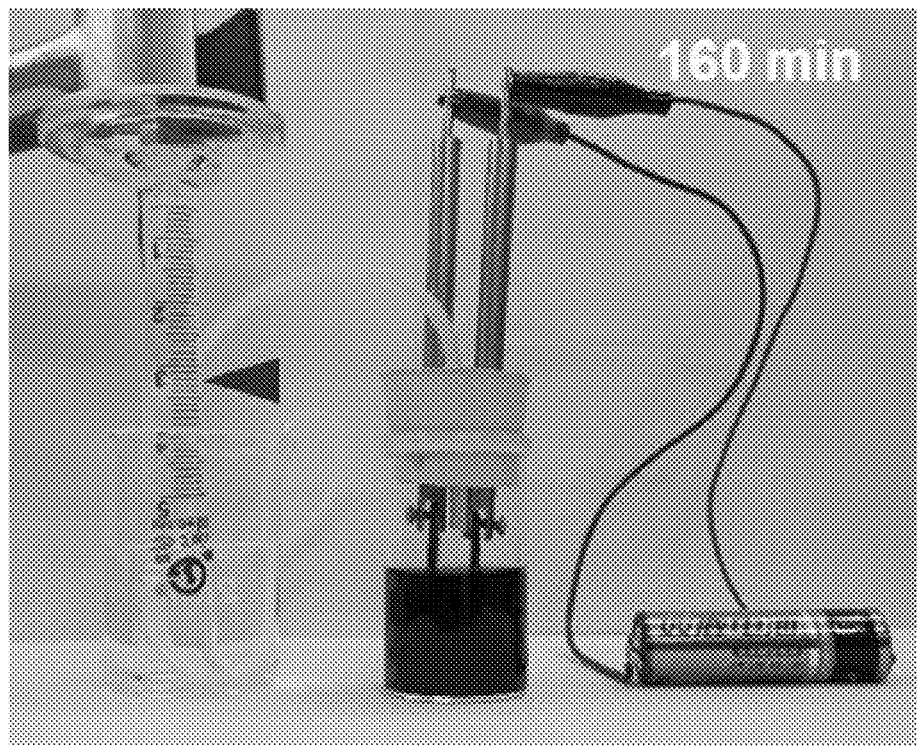
FIG. 6 shows the two-electrode electrocatalytic device used in the present application.
Figure 7:
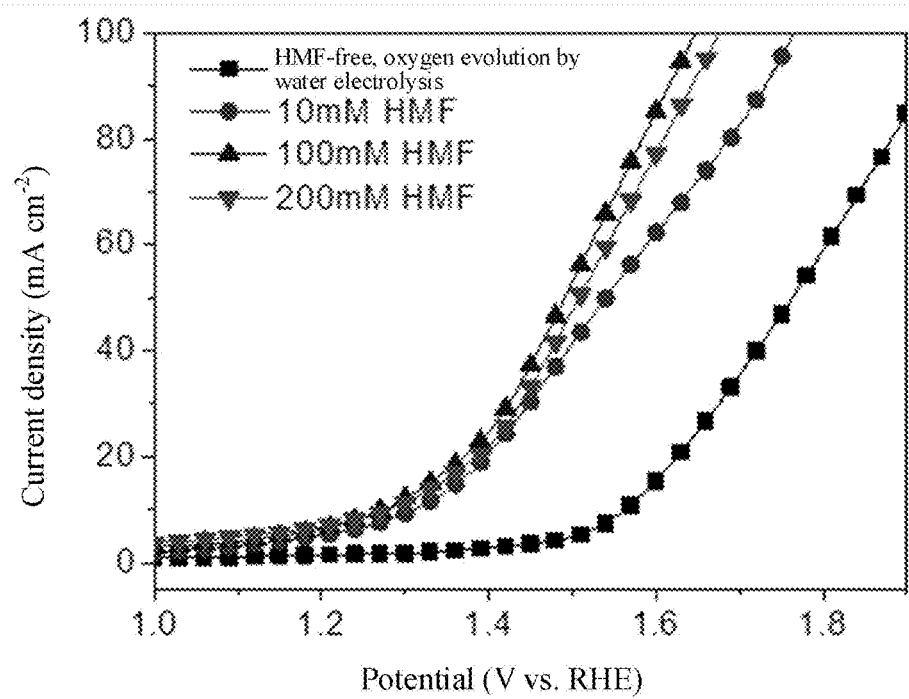
FIG. 7 shows anodic current density vs. potential curves of different electrolytes in a three-electrode system with Sample 1 prepared in Example 1 of the present application as an anodic catalyst.
Figure 8:
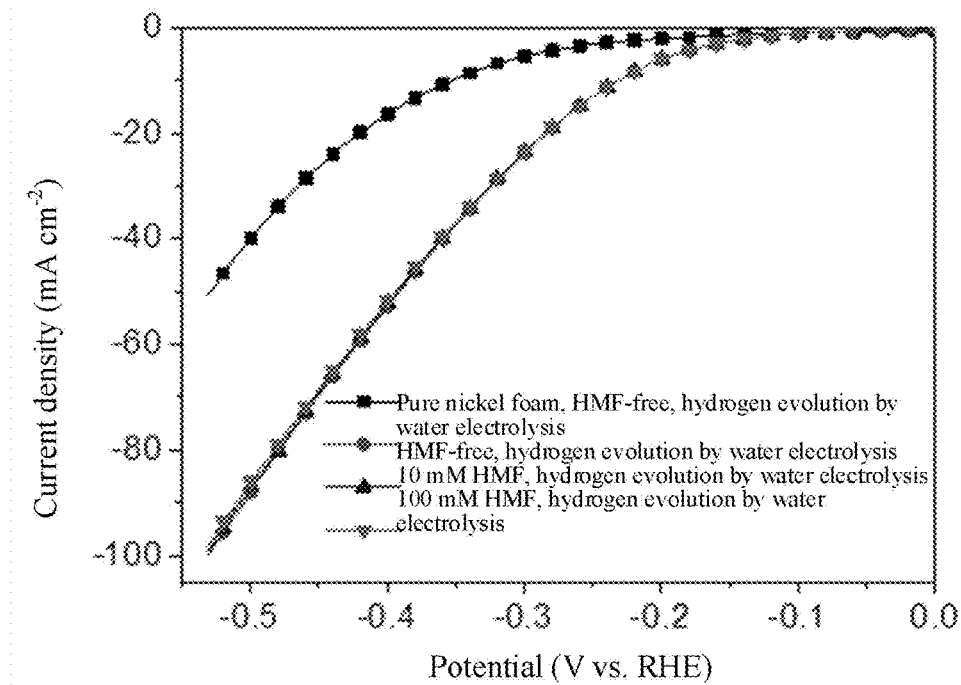
FIG. 8 shows cathodic current density vs. potential curves of different electrolytes in a three-electrode system with Sample 1 prepared in Example 1 of the present application as a cathodic catalyst.

A test device was shown in FIG. 6. An electrolytic cell including a power supply, an electrolyte, an anode, a cathode, and a current circuit was constructed, a voltage of 1.5 V was applied to conduct electrocatalysis, an electrolyte was placed in a closed reactor. The gas generated on the cathode was introduced into a gas collection device through a conduit, and the gas volume was obtained by the drainage method. When the electrolyte was a 100 mM HMF-containing sodium hydroxide aqueous solution, the electrocatalytic energy barrier was low, such that the coupled reaction could be driven by a commercial 1.5 V battery, and about 3.3 mL of hydrogen could be produced within 160 min. Typical test results were shown in FIG. 7 to FIG. 10, with sample 1 as an anodic catalyst. FIG. 7 shows that, in the three-electrode system, a monolithic cobaltosic oxide-encapsulated nitrogen-doped carbon nanowire catalyst is adopted as an anodic catalyst, which shows excellent performance in both oxygen evolution by water electrolysis without HMF and electrocatalytic oxidation of HMF to prepare FDCA, and can tolerate the feed of high-concentration HMF. FIG. 8 shows that, in the three-electrode system, the monolithic cobaltosic oxide-encapsulated nitrogen-doped carbon nanowire catalyst has a strong ability to produce hydrogen through water electrolysis, and the addition of HMF to the electrolyte does not affect the hydrogen production performance. Compared with the pure nickel foam anode, the cobaltosic oxide-encapsulated nitrogen-doped carbon nanowire anodic catalyst prepared in Example 1 of the present application has better hydrogen evolution performance in water electrolysis.

Figure 9:
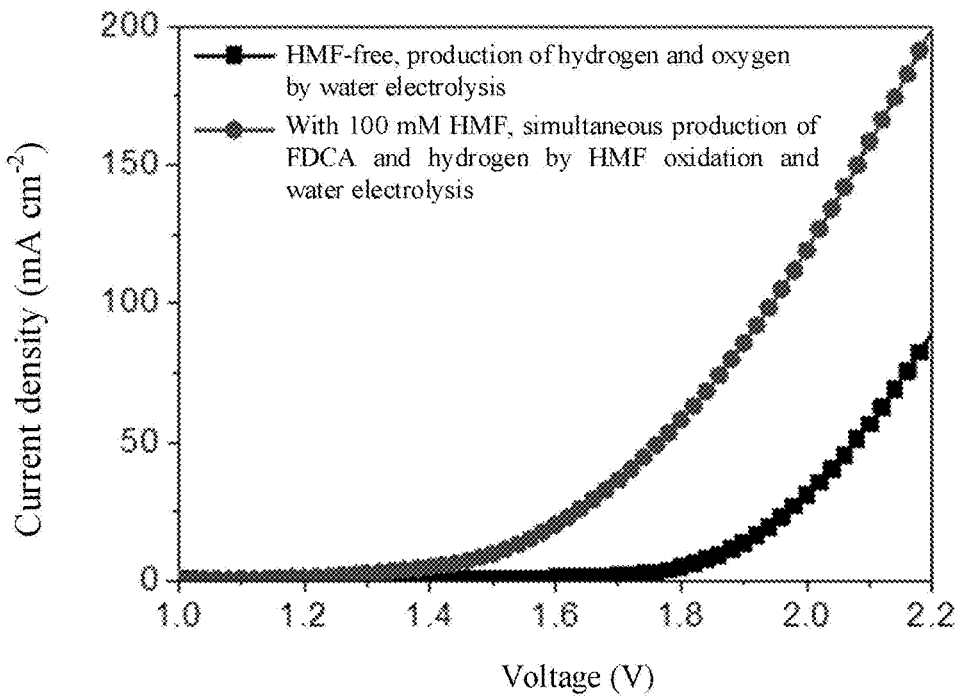
FIG. 9 shows current density vs. voltage curves for different electrolyte circuits in a two-electrode system with Sample 1 prepared in Example 1 of the present application as both a cathodic catalyst and an anodic catalyst.
Figure 10:
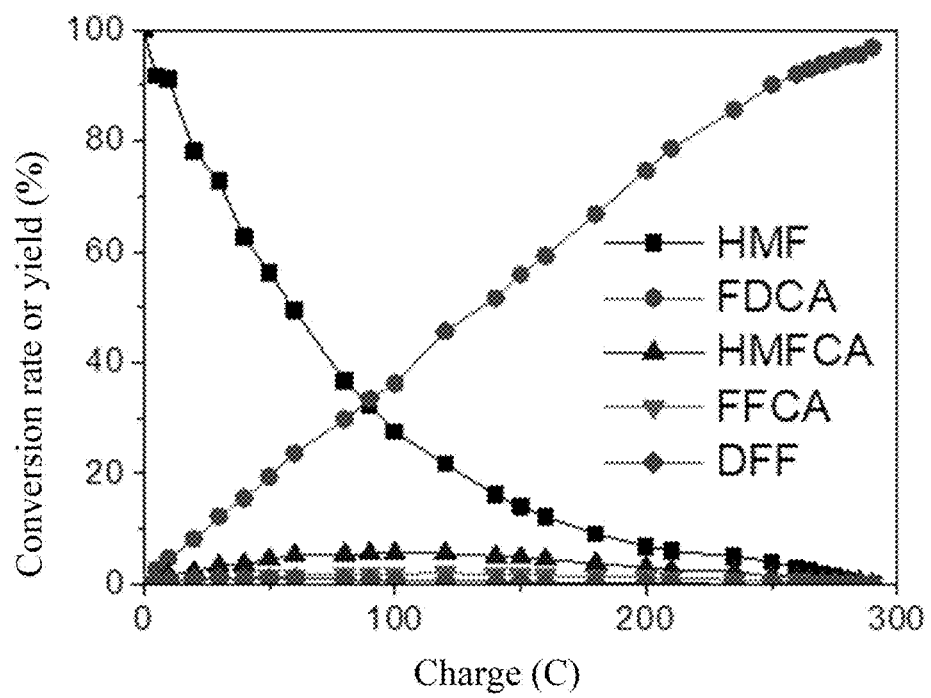
FIG. 10 shows raw material HMF conversion/anodic product yield vs. passing charge curves in a two-electrode system with Sample 1 prepared in Example 1 of the present application as both a cathodic catalyst and an anodic catalyst.

As shown in FIG. 9, the cobaltosic oxide-encapsulated nitrogen-doped carbon nanowire anodic catalyst prepared in Example 1 is used to assemble a two-electrode symmetric electrolytic cell, and the electrocatalytic oxidation of HMF to prepare FDCA and the water electrolysis to produce hydrogen are conducted simultaneously, which requires an overpotential 362 mV lower than that of simple water electrolysis, indicating a better catalytic performance with lower required energy compared to simple water electrolysis. As shown in FIG. 10, the cobaltosic oxide-encapsulated nitrogen-doped carbon nanowire catalyst prepared in Example 1 is used as both cathode and anode to assemble a two-electrode symmetric electrolytic cell to prepare FDCA by electrocatalytic oxidation of HMF, which shows extremely high FDCA selectivity and leads to high product purity. Moreover, the faradaic efficiency is close to 100%, with almost no energy waste.

When other samples are used as anodic catalysts, the similar catalytic effect can be achieved.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A method for producing 2,5-furandicarboxylic acid comprising conducting an electrocatalytic oxidation of 5-hydroxymethylfurfural (HMF) using an electrolytic cell and simultaneously generating hydrogen by a water electrolysis; wherein
    the electrolytic cell is a three-electrode electrolytic cell or a two-electrode electrolytic cell;
    an anode used in the electrolytic cell is a first monolithic electrode;
    the first monolithic electrode comprises a carrier and a catalytically active substance loaded on the carrier; and
    the catalytically active substance comprises cobaltosic oxide particle-encapsulated nitrogen-doped carbon nanowires.

2. The method according to claim 1, wherein an electrolyte in the electrolytic cell is an HMF-containing aqueous solution; and
    a concentration of the HMF in the HMF-containing aqueous solution is 0.001 mM to 500 mM.

3. The method according to claim 1, wherein the electrolytic cell has a voltage of 1.067 V to 2.0 V.

4. The method according to claim 1, wherein the three-electrode electrolytic cell has a minimum voltage of 1.067 V, and the two-electrode electrolytic cell has a minimum voltage of 1.175 V.

5. The method according to claim 1, wherein the hydrogen is simultaneously produced by the water electrolysis at a cathode of the electrolytic cell.

6. The method according to claim 1, wherein a cathode used in the electrolytic cell is at least one selected from the group consisting of a second monolithic electrode, a graphite rod, a platinum sheet, a platinum wire, a platinum mesh, a nickel sheet, a nickel wire, a nickel mesh, and a nickel alloy.

7. The method according to claim 1, wherein the catalytically active substance grows in situ on a surface of the carrier.

8. The method according to claim 1, wherein the catalytically active substance has a dendritic morphology formed by the cobaltosic oxide particle-encapsulated nitrogen-doped carbon nanowires.

9. The method according to claim 1, wherein the carrier is at least one selected from the group consisting of a metal foam, a carbon foam, and a carbon fiber sheet.

10. The method according to claim 1, wherein a cobaltosic oxide particle in the cobaltosic oxide particle-encapsulated nitrogen-doped carbon nanowires has a particle size of 3 nm to 10 nm; and the cobaltosic oxide particle-encapsulated nitrogen-doped carbon nanowires each have a diameter of 40 nm to 60 nm.

11. The method according to claim 1, wherein in the catalytically active substance, a molar content of nitrogen is 0.5% to 2%, a molar content of carbon is 20% to 40%, and a molar content of cobalt is 5% to 10%.

* * * * *